US009157834B2

(12) United States Patent
Beccavin et al.

(10) Patent No.: US 9,157,834 B2
(45) Date of Patent: Oct. 13, 2015

(54) HIGH VOLTAGE PROBE APPARATUS AND METHOD FOR TIRE INNER SURFACE ANOMALY DETECTION

(75) Inventors: Christian Albert Beccavin, Greenville, SC (US); Frank E. Gramling, Simpsonville, SC (US); David Andrew Judd, Mauldin, SC (US); Bradley D. Schober, Greer, SC (US)

(73) Assignees: MICHENLIN RECHERCHE et TECHNIQUE S.A., Granges-Paccot (CH); COMPAGNIE GENERAL DES ETABLISSEMENT MICHELIN, Clermont-Ferrano (FR)

( * ) Notice: Subject to any disclaimer, the term of this patent is extended or adjusted under 35 U.S.C. 154(b) by 256 days.

(21) Appl. No.: 13/822,092

(22) PCT Filed: Sep. 14, 2010

(86) PCT No.: PCT/US2010/048740
§ 371 (c)(1),
(2), (4) Date: Mar. 11, 2013

(87) PCT Pub. No.: WO2012/036673
PCT Pub. Date: Mar. 22, 2012

(65) Prior Publication Data
US 2013/0162265 A1 Jun. 27, 2013

(51) Int. Cl.
*G01M 17/02* (2006.01)
*G01N 27/20* (2006.01)
(Continued)

(52) U.S. Cl.
CPC .............. *G01M 17/02* (2013.01); *G01N 27/205* (2013.01); *G01M 3/40* (2013.01); *G01N 27/20* (2013.01); *G01R 31/022* (2013.01); *G01R 31/1263* (2013.01)

(58) Field of Classification Search
CPC . G01N 27/205; G01N 27/20; G01R 31/1263; G01R 31/022; G01M 3/40; G01M 17/02
USPC ............................................... 324/558; 73/146
See application file for complete search history.

(56) References Cited

U.S. PATENT DOCUMENTS 1,779,907 A * 10/1930 Dye ............................... 324/558
2,503,992 A * 4/1950 Becker .......................... 324/552
(Continued)

FOREIGN PATENT DOCUMENTS

EP         1939609 A1 *  7/2008  ............. G01N 23/04
JP         2000289416     10/2000
WO         2008/150894    12/2008

OTHER PUBLICATIONS
Related Applications Form.
(Continued)

*Primary Examiner* — Jermele M Hollington
*Assistant Examiner* — Christopher McAndrew
(74) *Attorney, Agent, or Firm* — Dority & Manning, P.A.

(57) ABSTRACT

A tire testing apparatus and method for detecting anomalies in the surface of a tire is disclosed. A high voltage probe having a conductive spring electrode is placed adjacent a portion of a tire surface such that the conductive spring electrode is compressed against the surface of the tire. Relative motion is imparted between the high voltage probe and the surface of the tire. An electrical discharge occurs between the high voltage probe and a reference electrode at the location of an anomaly on the surface of the tire. The apparatus and method are configured to determine a precise azimuthal and radial position on the tire of the electrostatic discharge. The conductive spring electrode can have a length sufficient to ensure contact with a given point on the tire surface during a charge cycle for the high voltage probe at increased tire surface speeds.

19 Claims, 7 Drawing Sheets

(51) Int. Cl.
*G01R 31/12* (2006.01)
*G01R 31/02* (2006.01)
*G01M 3/40* (2006.01)

(56) References Cited

U.S. PATENT DOCUMENTS

| | | | | |
|---|---|---|---|---|
| 2,626,982 | A * | 1/1953 | Collins | 324/558 |
| 4,260,889 | A * | 4/1981 | Osborn et al. | 378/61 |
| 4,491,013 | A * | 1/1985 | Bubik | 73/146 |
| 4,516,068 | A * | 5/1985 | Hawkinson et al. | 324/558 |
| 4,520,307 | A * | 5/1985 | Weiss et al. | 324/558 |
| 4,724,703 | A * | 2/1988 | Neugebauer et al. | 73/146 |
| 4,791,354 | A * | 12/1988 | Wardell | 324/717 |
| 6,050,136 | A | 4/2000 | Hawkinson et al. | |
| 6,304,090 | B1 | 10/2001 | Weiss | |
| 6,520,229 | B1 * | 2/2003 | Muraoka et al. | 152/152.1 |
| 6,600,326 | B2 | 7/2003 | Weiss | |
| 6,832,513 | B2 | 12/2004 | Weiss | |
| 6,837,102 | B2 | 1/2005 | Weiss | |
| 6,907,777 | B2 | 6/2005 | Weiss | |
| 7,257,996 | B2 | 8/2007 | Hassler et al. | |
| 7,826,192 | B2 * | 11/2010 | Sinnett et al. | 361/111 |
| 2003/0188573 | A1 * | 10/2003 | Weiss | 73/146 |
| 2003/0188574 | A1 * | 10/2003 | Weiss | 73/146 |
| 2004/0016293 | A1 * | 1/2004 | Weiss | 73/146 |
| 2005/0200493 | A1 * | 9/2005 | Marishak, Jr. | 340/652 |
| 2009/0078034 | A1 * | 3/2009 | Range et al. | 73/146 |
| 2009/0210032 | A1 * | 8/2009 | Beiski et al. | 607/59 |
| 2012/0077902 | A1 * | 3/2012 | Steiner et al. | 523/157 |
| 2012/0208919 | A1 * | 8/2012 | Kanz et al. | 523/156 |

OTHER PUBLICATIONS

International Search Report for PCT/US2010/048740, dated Nov. 5, 2010.

International Search Report for PCT/US2010/048743, dated Nov 5, 2010.

* cited by examiner

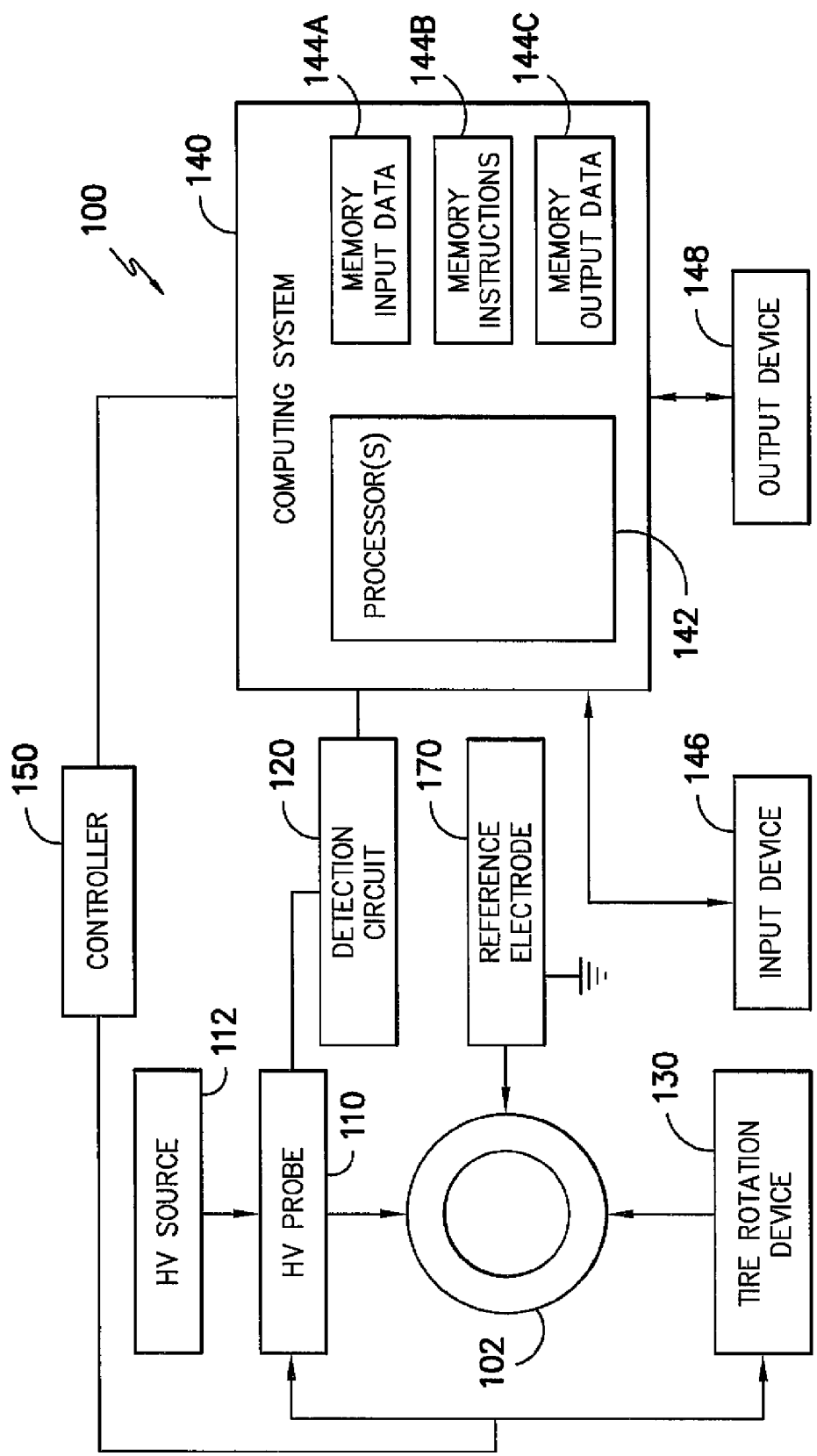
FIG. -1-

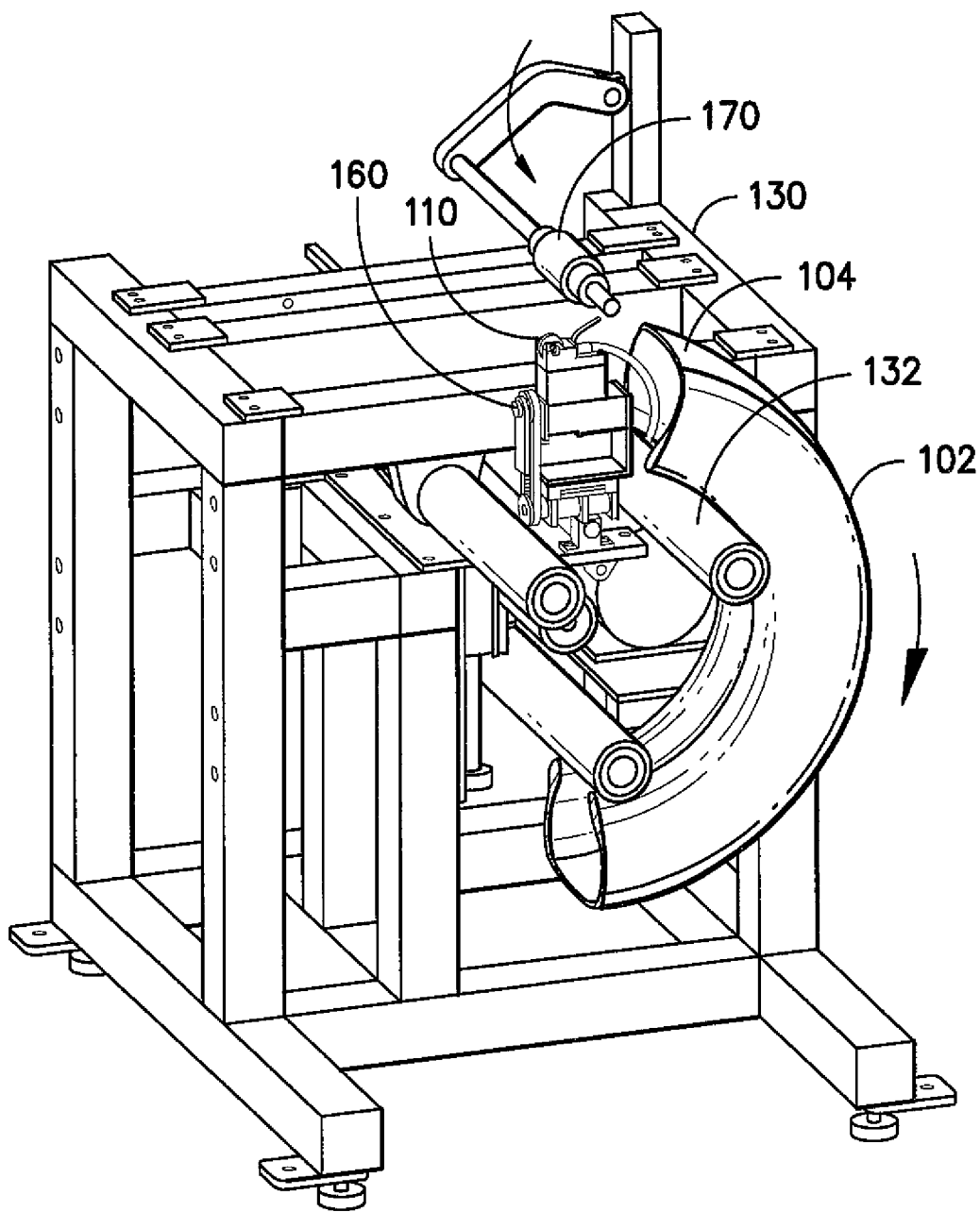
FIG. -2-

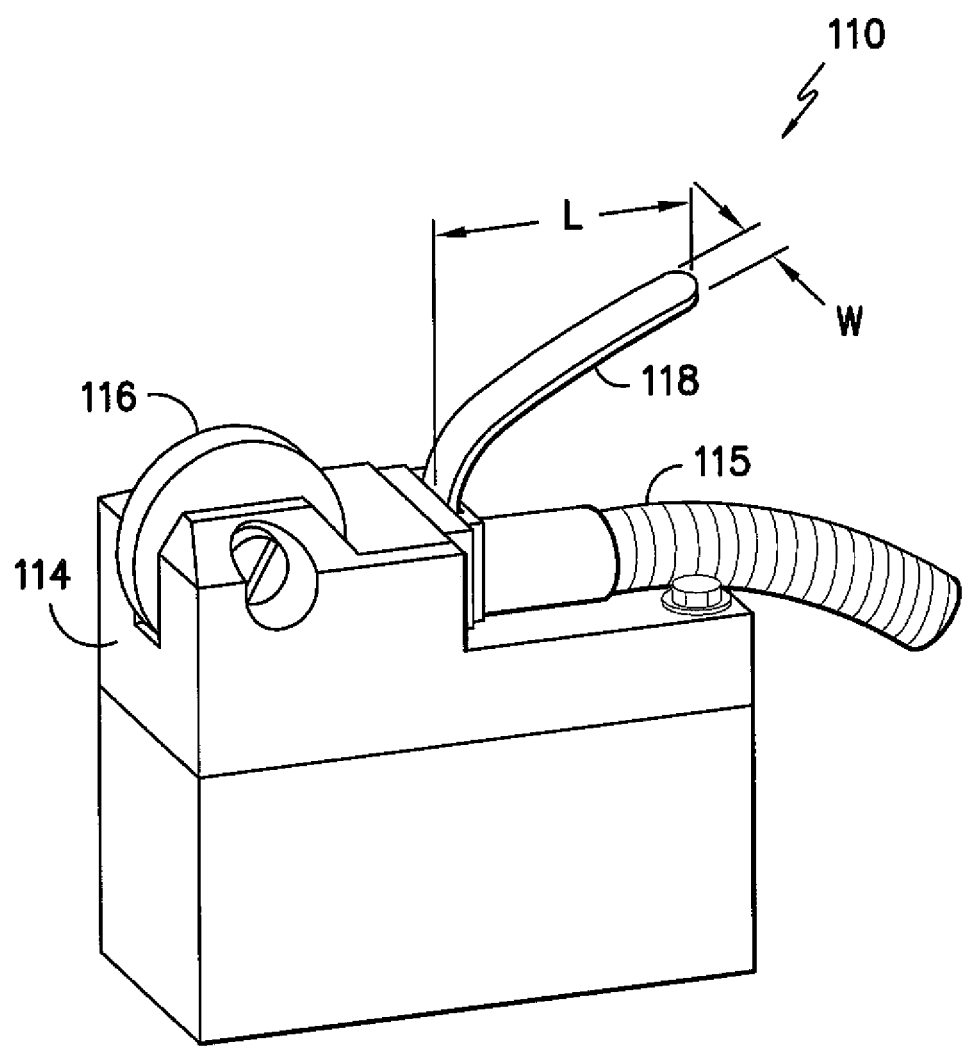
FIG. -3-

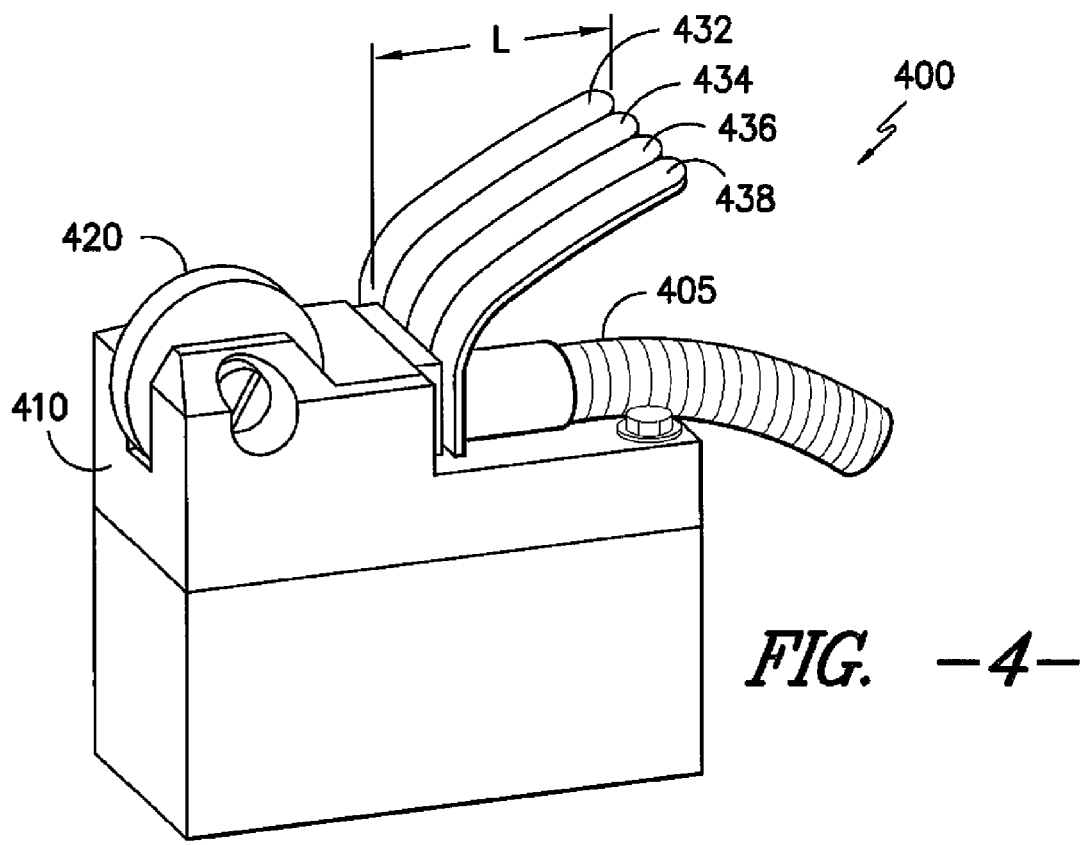
FIG. −4−
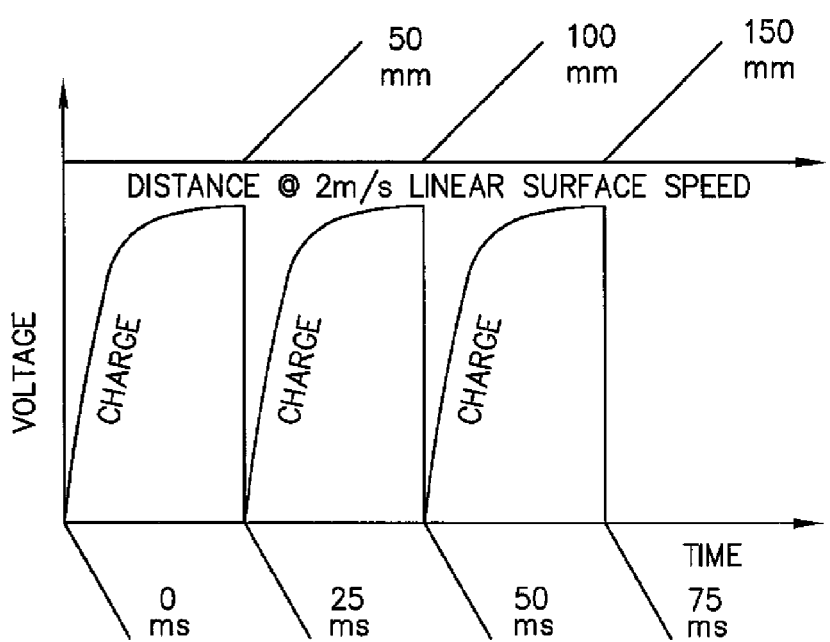
FIG. −5−

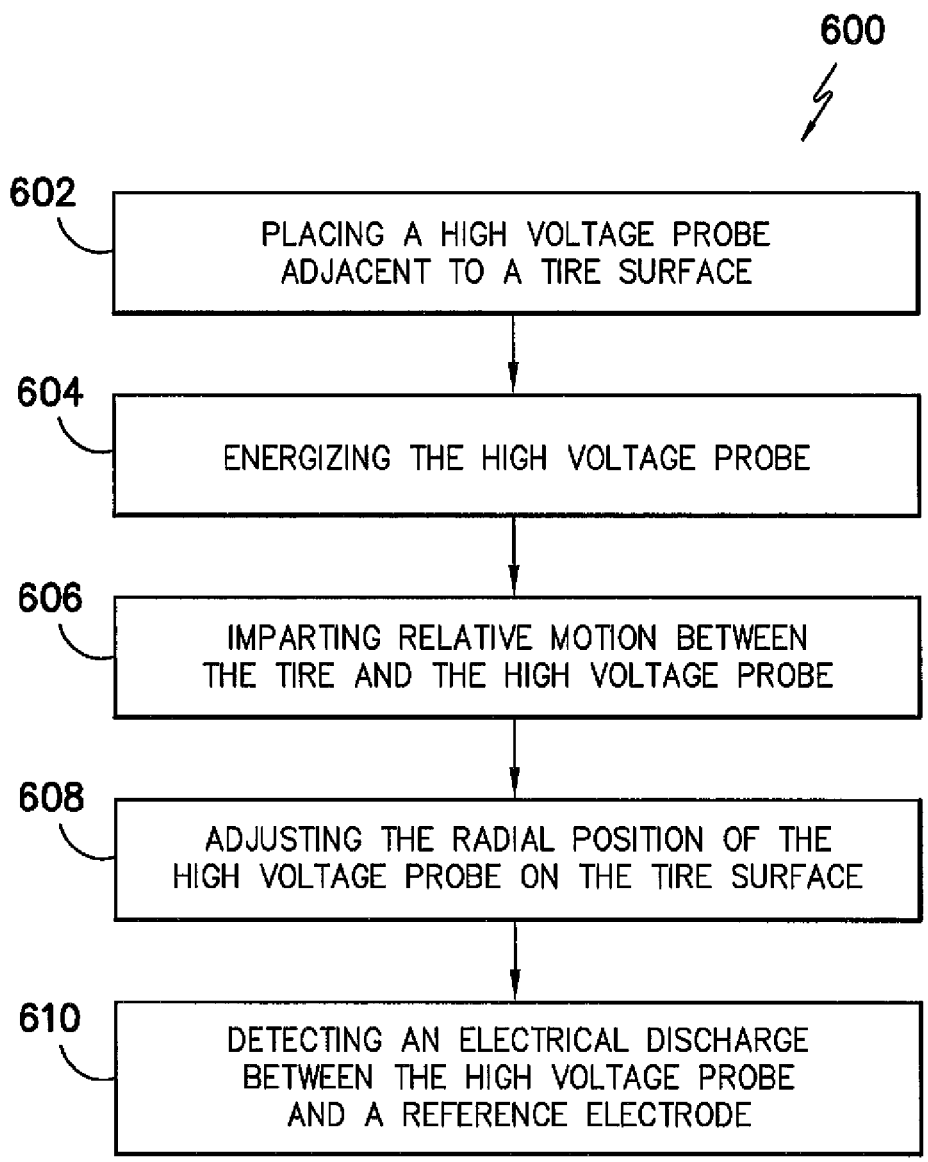
FIG. —6—

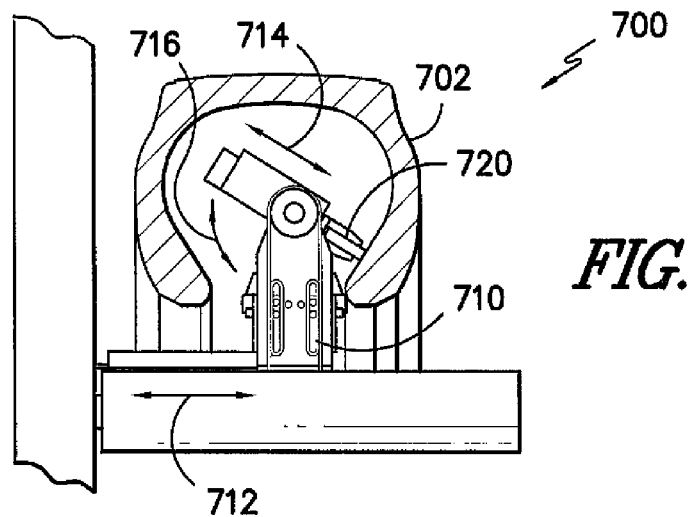
FIG. -7-
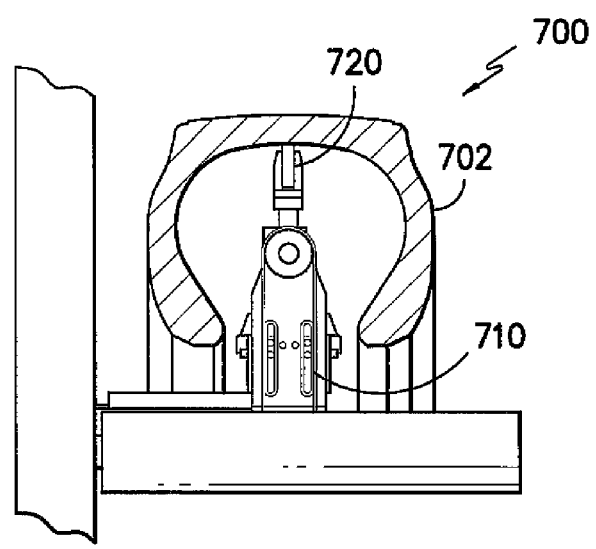
FIG. -8-
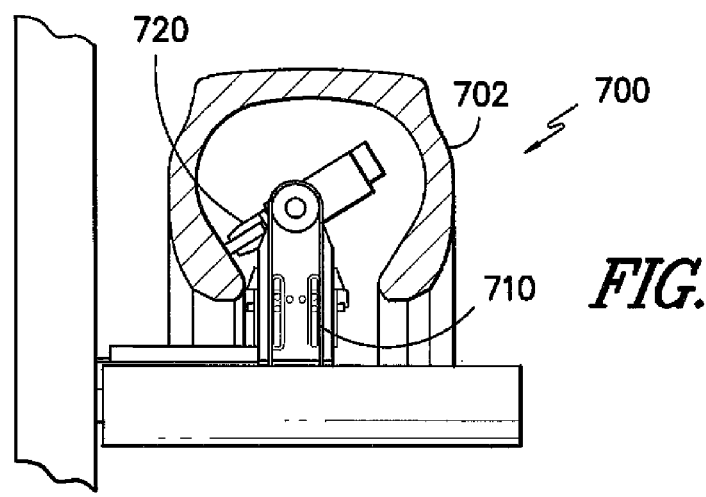
FIG. -9-

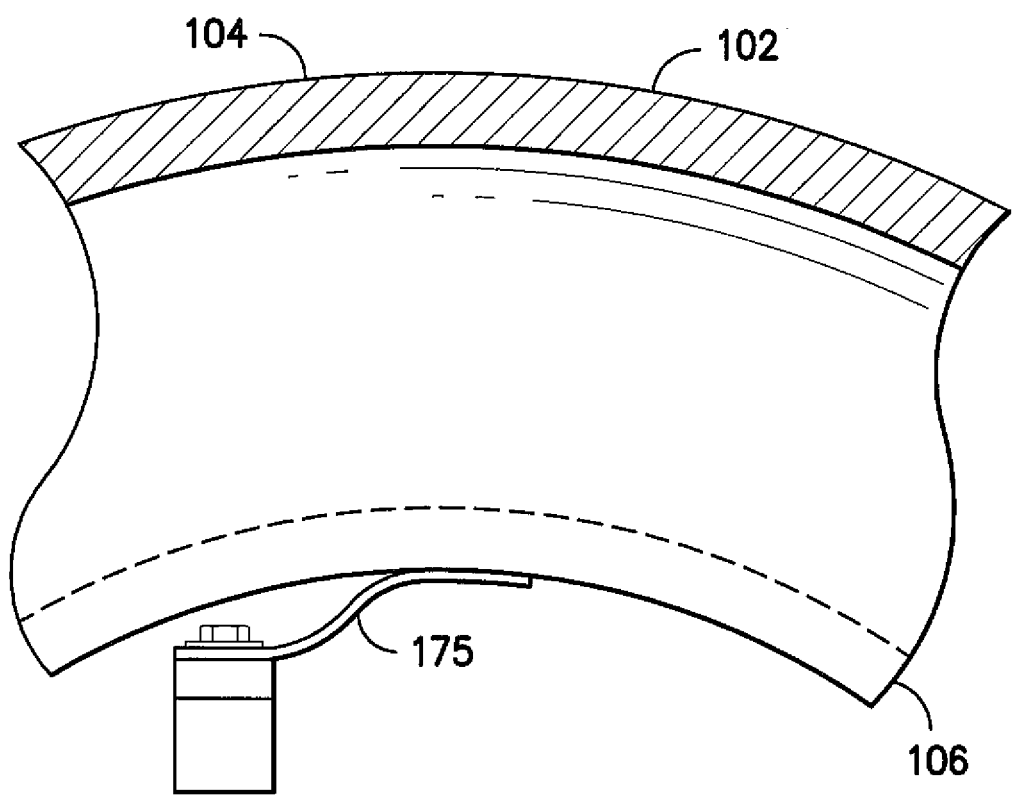
FIG. -10-

HIGH VOLTAGE PROBE APPARATUS AND METHOD FOR TIRE INNER SURFACE ANOMALY DETECTION

FIELD OF THE INVENTION

The present invention relates generally to tire testing, and more particularly to tire surface anomaly detection.

BACKGROUND OF THE INVENTION

Tire repair operations, such as tire retreading operations, are generally used to extend the useful service life of a tire. Typical tire retreading operations include removing previously worn tread from a tire and bonding new tread in its place. Tires may be retread or repaired one or more times as a less expensive alternative to purchasing new tires, providing particular advantages for large-scale operations such as trucking, bussing and commercial aviation.

Generally, some level of non-destructive testing (NDT) of the tire prior to repair is conducted to determine whether it is appropriate to perform the repair operation. Visual inspection methods can be used to validate the integrity and, subsequently, the viability of retread and/or repair of tire casings for retread. For instance, the inside and outside surface of a tire can be visually inspected by an operator using special lighting to inspect for defects such as crazing, cracks, snags, bulges, depressions, gouges, abrasions, marbling, bubbles, blisters, separations, and other defects. Visual inspection methods, however, are subjective, inconsistent, and can require extensive training. Moreover, due to high operator turnover, difficulty exists in retaining expertise.

High voltage discharge (HVD) testing can be performed in place of or supplemental to visual inspection. HVD testing can be used to identify anomalies in the inner liner of a tire that penetrate the insulating material of the inner liner. In HVD testing machines, the tread portion of a tire is typically disposed between a pair of electrodes across which a high voltage electrical potential is generated. The voltage applied across the electrode will cause electrical discharge at the location of a defect in a tire. U.S. Pat. No. 6,050,136, which is incorporated herein by reference for all purposes, for instance, discloses a HVD test machine that employs electrical discharging to detect defects in the inner liner of a tire.

On a traditional HVD test machine, the probe assembly typically includes a series of wire loops and small chains that are positioned to hang inside the tire in a manner to distribute high voltage from bead to bead on the inside surface of the tire. The correct width probe must be chosen for the tire size. The ground path for the discharge at an anomaly is provided by contact of the tread on a metallic driven roller. When the probe passes over an anomaly, an electrical discharge passes through the tread at the location of the anomaly to the metallic driven roller.

Traditional HVD test machines suffer from several disadvantages. For instance, traditional HVD test machines typically require manual selection of probe size to accommodate varying tire sizes. For instance, three different probe sizes may be provided to cover the range of retread capable truck tires. Once a probe size has been selected, the probe must be mounted semi-manually into the inner surface of the tire, causing the HVD testing machine to be susceptible to improper positioning.

In addition, because typical HVD probes cover the entire inside surface of the tire from bead to bead, when an anomaly is detected, it is unknown at what precise radial position the anomaly is located. Typically, the tire will stop rotating when a discharge is detected. This provides for an azimuth location of the anomaly. However, to obtain a precise radial location of the anomaly, the operator typically has to press and hold a manual button to repeat the discharge in order to mark the tire with a carbon deposit or to visually locate a corona discharge.

Furthermore, the detection capability of typical HVD test machines depends on many variables. For instance, the bend of the wires, the condition of the chains, the thickness of the tread, the speed of rotation, and the chemical makeup of the tread influence the detection capability of HVD test machines. Significant variability can occur with slight elevations changes of the tire surface, degradation or improper trimming of the chains, or degradation or improper positioning of the wires. For example, a slight elevation change in the inner surface of the tire may cause the HVD probe to temporarily leave the surface of the inner liner, causing the HVD probe to miss an anomaly in the tire surface.

Moreover, due to the cyclic charge and discharge nature of high voltage power sources used to energize HVD probes, detection of an anomaly is dependent on the probe being in close proximity to the anomaly when the high voltage charge is at a voltage level sufficient to discharge through an anomaly. The configuration of the chains and wires of the probe in relation to the tire dictates how much surface area of the probe is in contact with the tire. The tire surface must be rotated at a speed that is slow enough to ensure that the probe is sufficiently charged when the surface area of the probe is in contact with a given point on the tire surface to detect the presence of anomalies.

Thus, a solution is needed for automated HVD testing of tires that overcomes the above mentioned disadvantages. The solution can reduce the need for operator interaction to determine the accurate and precise location of tire surface anomalies. A high voltage probe that is less susceptible to variables, such as elevation changes in the surface of the tire and improper positioning of the high voltage probe, would be particularly useful. A high voltage probe that can be used with increased tire rotation speeds and that ensures contact with a given point on the surface of the tire when the high voltage probe is charged to a voltage level sufficient to discharge through an anomaly would also be particularly useful.

SUMMARY OF THE INVENTION

Aspects and advantages of the invention will be set forth in part in the following description, or may be obvious from the description, or may be learned through practice of the invention.

One exemplary embodiment of the present disclosure is directed to a tire inspection apparatus. The tire inspection apparatus includes a high voltage probe operable to be positioned adjacent a surface of a tire. The apparatus further includes a reference electrode and a tire rotation device operable to impart relative motion between the surface of the tire and the high voltage probe. The tire inspection apparatus further includes a detection circuit operable to detect one or more electrical discharges between the high voltage probe and the reference electrode. The high voltage probe includes a conductive spring electrode configured to be compressed against the surface of the tire during a tire inspection process. In a particular embodiment, the high voltage probe can include a plurality of adjacent spring electrodes. Each of the plurality of spring electrodes can be configured to be compressed against a portion of the surface of the tire during a tire inspection process.

In a variation of this exemplary embodiment, the conductive spring electrode has a length sufficient to maintain contact with a point on the surface of the tire during a charge cycle for the high voltage probe. For instance, in a particular embodiment, the conductive spring electrode can have a length of about 50 mm.

In another variation of this exemplary embodiment, the tire inspection apparatus can further include a high voltage probe positioning device operable to position the high voltage probe adjacent the tire surface such that the conductive spring electrode is compressed against the surface of the tire at a first radial position. The high voltage probe positioning device can be further configured to adjust the high voltage probe from the first radial position to a second radial position. The second radial position can be immediately adjacent to the first radial position.

In yet another variation of this exemplary embodiment, the reference electrode of the tire inspection apparatus can be positioned adjacent a tread portion of the tire. In a further variation of this exemplary embodiment, the reference electrode can be positioned adjacent a bead portion of the tire.

In still a further variation of this exemplary embodiment, the tire inspection apparatus further comprises a detection circuit operable to provide a signal representative of the azimuthal and radial position of the one or more electrical discharges on the surface of the tire. The signal representative of the one or more electrical discharges can be used to determine the precise location of one or more anomalies on the tire surface.

Another exemplary embodiment of the present disclosure is directed to a tire inspection method. The tire inspection method includes positioning a high voltage probe adjacent a surface of a tire. The high voltage probe has a conductive spring electrode configured to be compressed against the surface of the tire. The method further includes energizing the high voltage probe; imparting relative motion between the high voltage probe and the surface of the tire; and detecting one or more electrical discharges between the high voltage probe and a reference electrode to detect the presence of one or more anomalies on the surface of the tire.

In a variation of this exemplary embodiment, imparting relative motion between the high voltage probe and the surface of the tire can include rotating the surface of tire about the high voltage probe with a tire rotation device. In another variation of this exemplary embodiment, the method can further include adjusting the radial position of the high voltage probe. For instance, in a particular embodiment, imparting relative motion between the high voltage probe and the surface of the tire can include positioning the high voltage probe such that the conductive spring electrode is compressed against the surface of the tire at a first radial position; rotating the surface of the tire about the surface of the high voltage probe for at least one revolution; positioning the high voltage probe such that the conductive spring electrode is compressed against the surface of the tire at a second radial position; and rotating the surface of the tire about the surface of the high voltage probe for at least one revolution. The first radial position can be immediately adjacent to the second radial position.

In a further variation of this exemplary embodiment, the tire inspection method can include monitoring the location of the one or more electrical discharges on the surface of the tire. The location of the one or more electrical discharges can indicate the presence of one or more anomalies on the surface of the tire.

In yet a further variation of this exemplary embodiment, the method can include positioning the reference electrode adjacent a tread portion of the tire. In still a further variation of this exemplary embodiment, the method can include positioning the reference electrode adjacent a bead portion of the tire.

A further exemplary embodiment of the present disclosure is directed to a high voltage probe for use in a tire inspection apparatus. The high voltage probe includes an insulating casing, a spacing roller, a high voltage connection point, and a conductive spring electrode. The conductive spring electrode is adapted to be compressed against a portion of a tire surface when the spacing roller contacts the surface of a tire.

In a variation of this exemplary embodiment, the conductive spring electrode has a length sufficient to maintain contact with a point on the surface of the tire during a charge cycle for the high voltage probe. For instance, in a particular embodiment the conductive spring electrode has a length of about 50 mm.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. -1- illustrates a block diagram of an exemplary tire inspection system according to an exemplary embodiment of the present disclosure;

FIG. -2- illustrates a perspective view of an exemplary tire testing apparatus according to an exemplary embodiment of the present disclosure;

FIG. -3- illustrates a perspective view of an exemplary high voltage probe according to an exemplary embodiment of the present disclosure FIG. -4- illustrates a perspective view of an exemplary high voltage probe according to another exemplary embodiment of the present disclosure;

FIG. -5- illustrates a graphical representation of exemplary charge cycles for a high voltage probe according to an exemplary embodiment of the present disclosure;

FIG. -6- illustrates a flow chart of exemplary method steps according to an exemplary embodiment of the present disclosure;

FIG. -7- illustrates a high voltage probe maintained at a first radial position on the surface of a tire according to an exemplary embodiment of the present disclosure;

FIG. -8- illustrates a high voltage probe maintained at a second radial position on the surface of a tire according to an exemplary embodiment of the present disclosure;

FIG. -9- illustrates a high voltage probe maintained at a third radial position on the surface of a tire according to an exemplary embodiment of the present disclosure; and FIG. -10- illustrates an exemplary reference electrode that can be used in accordance with an alternate embodiment of the present disclosure.

DETAILED DESCRIPTION OF THE INVENTION

For purposes of describing the invention, reference now will be made in detail to embodiments and aspects of the invention, one or more examples of which are illustrated in the drawings. Each example is provided by way of explanation of the invention, not limitation of the invention. In fact, from the teachings disclosed herein, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Generally, the present disclosure is directed to HVD testing for anomalies on a surface of a tire. In particular embodiments, a high voltage probe having a conductive spring electrode is maintained against the surface of a tire such that the conductive spring electrode is compressed against the tire surface. The conductive spring electrode is energized and relative motion is provided between the surface of the tire and the high voltage probe. At the presence of an anomaly that penetrates the insulating material of the tire surface, an electrical discharge will occur between the conductive spring electrode and a reference electrode.

The high voltage probe according to embodiments of the present disclosure provides various advantages over HVD testing machines known in the art. For example, the high voltage probe can be automatically presented to the entire surface of the tire, from bead to bead, reducing errors caused by improper positioning of the high voltage probe. Moreover, the high voltage probe can be used to test tires of multiple different sizes without having to use different sized high voltage probes.

As another example, embodiments of the present disclosure can provide for the precise indication of the azimuthal and radial position of an anomaly on the tire surface. For instance, the high voltage probe can be first disposed adjacent a tire surface at a particular radial position. As the tire rotates about the high voltage probe, an electrical discharge may occur between the high voltage probe and a reference electrode at the location of an anomaly. Because the high voltage probe is disposed at a particular radial and azimuthal position when the discharge occurs, the precise radial and azimuthal location of an anomaly can be easily determined.

As yet another example, when the conductive spring electrode is compressed against the surface of the tire, the tire testing system is less susceptible to errors caused by elevation changes in the inner surface of the tire. For instance, if the conductive spring electrode passes over a small elevation change on the surface of a tire, the elasticity of the conductive spring electrode will cause the surface of the conductive spring electrode to be maintained against the surface of the tire. In this manner, the conductive spring electrode reduces errors in anomaly detection due to slight elevation changes in the surface of the tire.

As still another example, the conductive spring electrode is specifically sized to enhance anomaly detection capability. For instance, the width of the spring electrode is preferably configured so that each successive positioning of the high voltage probe against the tire surface will not miss any anomalies. In addition, the length of the conductive spring electrode can be configured to ensure that an electrode charged to a voltage level sufficient to discharge through an anomaly is applied to the entire surface of the tire at increased tire rotation speeds. In this manner, embodiments of the present disclosure provide for more efficient automated high voltage discharge testing of tires with reduced dependency on variables such as speed of rotation, elevation changes on the tire surface, and improper positioning of the high voltage probe.

Referring to FIG. -1-, a schematic overview of an exemplary tire testing system 100 according to an exemplary embodiment of the present disclosure will now be set forth. Tire testing system 100 can be used to perform HVD testing techniques to a tire 102 to determine the presence of one or more surface anomalies in the tire 102, and to determine whether tire 102 is viable for repair or retread. As used herein, the term "anomaly" can refer to any irregularity in the surface of a tire, including defects in the tire such as crazing, cracks, snags, gouges, abrasions, penetrations and other defects.

Tire testing system 100 can include a high voltage probe 110, a detection circuit 120, a tire rotation device 130, and a reference electrode 170. A high voltage source 112 can provide high voltage energy, such as about 37.5 kV to about 50 kV DC voltage energy, to high voltage probe 110. High voltage source 112 can be any source configured to provide high voltage energy to high voltage probe 110. For instance, in a particular embodiment, high voltage source 112 can include a TEI Micro FS-D unit that utilizes a charge/discharge cycle for producing 50 kV DC at the high voltage probe. Those of ordinary skill in the art, using the disclosures provided herein, should understand that any high voltage source can be used without deviating from the scope of the present disclosure.

High voltage probe 110 can be maintained against the surface of tire 102 using a high voltage probe positioning device. The high voltage probe positioning device can be controlled by controller 150 to automatically position the high voltage probe 110 against the surface of the tire 102. Tire rotation device 130 can be controlled by controller 150 to impart relative motion between the high voltage probe 110 and the surface of tire 102. For instance, tire rotation device 130 can be used to rotate the inner surface of a tire over high voltage probe 110. When the high voltage probe 110 passes over an anomaly that penetrates the inner surface of the tire, an electrical discharge will occur between the high voltage probe 110 and the reference electrode 170. The location of the electrical discharge provides an indication of the location of an anomaly in the inner surface of tire 102.

Detection circuit 120 can be used to detect the presence of an electrical discharge between the high voltage probe 110 and the reference electrode 170. A variety of detection circuits 120 for detecting electrical discharges are known. Any known detection circuit 120 for detecting an electrical discharge between high voltage probe 110 and the reference electrode 170 can be used without deviating from the scope of the present disclosure. For instance, in a particular embodiment, detection circuit can include an off the shelf component from TEI. Detection circuit 120 can include various electronic devices to monitor the voltage and/or voltage frequency at the high voltage probe 110. Changes in the voltage and/or frequency at the high voltage probe 110 can indicate the presence of an electrical discharge. Detection circuit 120 can be coupled with azimuthal and radial feedback circuits that provide position feedback signals indicating the precise azimuthal and radial location of the electrical discharge. In this manner, detection circuit 120 can provide data associated with the occurrence and precise location an electrical discharge to computing system 140.

Computing system 140 can be used to control, through controller 150, various aspects of system 100, as well as to store and analyze information received from detection circuit 120 during a tire inspection process. In particular, computing system 140 can include one or more processor(s) 142 configured to receive input data including data from detection circuit 120 and to provide useable output such as data to a user or signals to process controller 150. For instance, in a particular embodiment, processor(s) 142 can use data received from detection circuit 120 to generate a graphical representation, such as a two-dimensional map or other suitable graphical representation, of the tire surface.

Various memory/media elements 144 can be provided as a single or multiple portions of one or more varieties of computer-readable media, such as, but not limited to, any combination of volatile memory (e.g., random access memory (RAM, such as DRAM, SRAM, etc.) and nonvolatile memory (e.g., ROM, flash, hard drives, magnetic tapes, CD-ROM, DVD-ROM, etc.) or any other memory devices including diskettes, drives, other magnetic-based storage media, optical storage media and others. Although FIG. -1- shows three separate memory/media elements 144a, 144b and 144c, the content dedicated to such devices may actually be stored in one memory/media element or in multiple elements. Any such possible variations and other variations of data storage, using the disclosures provided herein, will be appreciated by one of ordinary skill in the art.

The computing/processing devices of FIG. -1- may be adapted to function as a special-purpose machine providing desired functionality by accessing software instructions rendered in a computer-readable form stored in one or more of the memory/media elements (e.g., memory/media element 144b). When software is used, any suitable programming, scripting, or other type of language or combinations of languages may be used to implement the teachings contained herein. In other embodiments, the methods disclosed herein may alternatively be implemented by hard-wired logic or other circuitry, including, but not limited to application-specific circuits.

Other memory/media elements (e.g., memory/media elements 144a, 144c) are used to store data which will also be accessible by the processor(s) 142 and which will be acted on per the software instructions stored in memory/media element 144b. For example, memory/media element 144a can include input data corresponding to the occurrence and location of electrical discharges obtained from the detection circuit 120 as well as any predetermined parameters, such as but not limited to, control parameters, such as high voltage probe parameters, detection circuit parameters, tire rotation parameters, other suitable control parameters, and tire parameters, such as tire radius, tire width, tire summit mass, tire pressure, tire radial stiffness, tire tangential stiffness, tire bending stiffness, tire extensional stiffness, tread locations, general tire data and the like. Such predetermined parameters may be pre-programmed into memory/media element 144a or provided for storage therein when entered as input data from a user accessing the input device 146.

Input device 146 may correspond to one or more peripheral devices configured to operate as a user interface with image processing system 140. Exemplary input devices may include but are not limited to a keyboard, touch-screen monitor, microphone, mouse and other suitable input devices.

Second memory element 144b can include computer-executable software instructions that can be read and executed by processor(s) 142 to act on the input data stored in memory/media element 144a to create new output data (e.g., anomaly identification and location) for storage in a third memory/media element 144c. Selected portions of the output data may then be provided to one or more peripheral output devices 148.

Output device 148 may correspond to a display such as a monitor, screen, or other visual display, a printer, or the like. Another specific form of output device may correspond to a process controller 150. In one embodiment, process controller 150 assists the overall tire manufacturing process by coordinating operating parameters of high voltage probe 110, a high voltage probe positioning device, tire rotation device 130, and other process parameters.

Referring to FIG. -2-, an exemplary arrangement of a tire 102, tire rotation device 130, and high voltage probe 110 will be discussed in detail. As illustrated, tire rotation device 130 includes one or more rollers 132. The bead portion of tire 102 rests on one or more rollers 132. The rollers 132 are configured to impart motion to tire 102, for instance by continuously rotating the inner surface of tire 102 over high voltage probe 110. Tire 102 is placed over the top of a high voltage probe 110 so that high voltage probe 110 can test the inner surface of tire 102 for anomalies.

As will be discussed in more detail below, high voltage probe positioning device 160 is used to position high voltage probe 110 adjacent a first radial position on the inner surface of tire 102. Tire rotation device 132 rotates the tire 102 over the high voltage probe 110 for at least one complete tire revolution. The high voltage probe positioning device 160 can then be used to position the high voltage probe 110 adjacent a second radial position on the inner surface of tire 102. Tire rotation device 130 then rotates tire 102 over the high voltage probe for at least one complete tire revolution. The process is repeated until the entire inner surface from bead to bead of the tire 102 has been tested for anomalies.

A reference electrode 170 is disposed adjacent the tread portion 104 of tire 102. Reference electrode 170 includes a conductive roller that rotates along the surface of tread portion 104 of tire 102 as tire 102 is rotated in tire rotation device 130. Reference electrode 170 is coupled to a reference voltage, such as a ground potential. When the high voltage probe 110 passes over an anomaly in the inner surface of tire 102, an electrical discharge occurs between high voltage probe 110 and reference electrode 170 through tread portion 104.

FIG. -3- provides a perspective view of an exemplary high voltage probe 110 that can be used in accordance with exemplary aspects of the present disclosure. High voltage probe 110 includes a high voltage connection point 115 for connecting the high voltage probe 110 to a high voltage energy source. Any suitable connection to a high voltage energy source can be used without deviating from the scope of the present disclosure. For instance, the high voltage connection point 115 can be adapted to receive a shielded, flexible high voltage cable from a high voltage source.

High voltage probe 110 further includes an insulating casing 114, a spacing roller 116, and a conductive spring electrode 118. Insulating casing 114 can be composed of any material sufficient to insulate high voltage energy such as, for instance, about 50 kV DC. Insulating casing 114 is used to insulate various components of high voltage probe 110 and other components of the tire testing apparatus from an energized conductive spring electrode 118.

Conductive spring electrode 118 is used to apply high voltage energy to the inner surface of a tire. Conductive spring electrode 118 has a shape and configuration adapted to be compressed against the surface of the tire when spacing roller 116 maintains contact with the tire surface. As the conductive spring electrode 118 is compressed, the elasticity of the conductive spring electrode 118 causes the conductive spring electrode 118 to maintain contact with the tire surface, even when the conductive spring electrode 118 passes over slight elevations in the tire surface. In this manner, the tire testing apparatus is not susceptible to errors caused by slight elevation changes in the tire surface and provides for more accurate detection of anomalies.

Conductive spring electrode 118 can be constructed of any suitable conductive material. For instance, in a particular embodiment, conductive spring electrode 118 is composed of steel. However, other suitable conductors, such as aluminum, copper, gold, etc., can be used to construct conductive spring electrode 118 as desired.

As illustrated, conductive spring electrode 118 has a width W. Unlike high voltage probes known in the art, conductive spring electrode 118 only contacts a limited portion of a tire surface equivalent to width W of conductive spring electrode 118. As will be discussed in detail below, due to its limited width W, conductive spring electrode 118 is maintained adjacent to a specific radial position of a tire surface during a tire inspection process. By maintaining the conductive spring electrode 118 at a specific radial position on the surface of a tire, the precise radial position of an electrical discharge from the conductive spring electrode 118 can be determined. Preferably, the width W of the conductive spring electrode 118 should be set such that each successive positioning of the high voltage probe 110 by a high voltage probe positioning device during an automated tire inspection process does not miss any portions of the tire surface.

Conductive spring electrode 118 also has a specified length L. In particular embodiments, conductive spring electrode 118 has a length L sufficient to maintain contact with a given point on a tire surface during a complete charge cycle for high voltage probe 110. In particular, a high voltage source used to energize high voltage probe 110 can utilize a charge/discharge cycle for producing high voltage at the conductive spring electrode 118. For instance, in a particular embodiment, the charge/discharge cycle can occur at about 40 times per second. Because the discharge is almost instantaneous, the time to recharge the probe can take up to about 25 milliseconds. It is desirable to maintain the conductive spring electrode 118 adjacent to a given point on the tire surface during the entire 25 millisecond charge cycle to ensure that the conductive spring electrode 118 is at a voltage sufficient to discharge through an anomaly when it passes over the point on the tire surface. This can be achieved by rotating the tire at a speed slow enough to allow the conductive spring electrode 118 to recharge to a high voltage before completely passing over the point on the surface of the tire. However, it is often desirable to increase the speed of rotation during the tire inspection process to provide for the quicker automated testing of tires. Thus, reducing tire speed is not always a feasible solution.

To allow for faster rotation speeds, conductive spring electrode 118 has a length L sufficient to allow conductive spring electrode 118 to completely recharge to a voltage level sufficient to discharge through an anomaly before completely passing over a given point on a tire surface. For instance, FIG. -5- depicts a graphical illustration of a recharge cycle for an exemplary high voltage probe. As illustrated, it takes approximately 25 milliseconds for the high voltage probe to completely recharge. FIG. -5- further depicts that at a linear tire surface speed of 2 m/s relative to the high voltage probe, a conductive spring electrode 118 having a length L of about 50 mm is sufficient to maintain contact with a given point on a surface of a tire during the 25 ms charge cycle for the high voltage probe. By ensuring that the high voltage probe 110 is completely charged to a voltage sufficient to discharge through an anomaly when passing over any given point on the surface of the tire, the accuracy of anomaly detection is further increased.

FIG. -4- illustrates an alternative embodiment of a high voltage probe 400 that can be used in accordance with the present disclosure. Similar to high voltage probe 110 of FIG. -3-, high voltage probe 400 of FIG. -4- includes a high voltage connection point 405 for connecting the high voltage probe 400 to a high voltage energy source. High voltage probe 400 further includes an insulating casing 410 and a spacing roller 420. In contrast to high voltage probe 110 of FIG. -3-, however, high voltage probe 400 includes a plurality of adjacent conductive spring electrodes 432, 434, 436, and 438. While four conductive spring electrodes 432, 434, 436, and 438 are illustrated in FIG. -4-, more or less conductive spring electrodes can be used as desired. Each of the plurality of conductive spring electrodes 432, 434, 436, and 438 is configured to be compressed against a portion of the surface of the tire during a tire inspection process. By using a plurality of conductive spring electrodes 432, 434, 436, and 438, high voltage probe 400 can scan a greater portion of the tire surface during each successive pass of the tire surface about the high voltage probe 400. In this manner, less tire rotations are required to scan the entire surface of the tire, leading to quicker tire inspection time.

With reference now to FIGS. -6-, an automated tire testing method 600 for inspecting a surface of a tire for anomalies will now be discussed. At 602, the method 600 includes placing a high voltage probe adjacent to the tire surface. For instance, as will be discussed in more detail below, a high voltage probe positioning device can position the high voltage probe such that a conductive spring electrode on the high voltage probe is compressed against the surface of the tire. At 604, the method 600 includes energizing the high voltage probe with a high voltage. For instance, a high voltage source can provide a high voltage, such as from about 37.5 kV to about 50 kV DC, to the high voltage probe.

Once the high voltage probe is energized, the method 600 includes imparting relative motion between the tire and the high voltage probe as shown at 606. This can be performed by either rotating the surface of the tire about the high voltage probe or by rotating the high voltage probe around the surface of the tire. A tire rotation device, such as tire rotation device 130 of FIG. -2- can be used to rotate an inner surface of a tire about a high voltage probe. At 608, the method 600 includes adjusting the radial position of the high voltage probe on the tire surface. This can be accomplished in an automated process using a high voltage probe positioning device as will be discussed in more detail with reference to FIGS. -7-, -8-, and -9-.

In a particular embodiment, the radial position of the high voltage probe is adjusted after a complete revolution of the tire about the high voltage probe. For instance, the method 600 can include positioning the high voltage probe such that a conductive spring electrode is compressed against the surface of the tire at a first radial position. The method 600 then rotates the surface of the tire about the high voltage probe for at least one revolution. The method 600 then positions the high voltage probe such that the conductive spring electrode is compressed against the surface of the tire at a second radial position. Preferably, the second radial position is immediately adjacent to the first radial position. The method 600 then rotates the surface of the tire about the high voltage probe a second time for at least one revolution. In this manner, the high voltage probe can be used to scan the entire inner surface of the tire from bead to bead.

At 610, the method 600 includes detecting an electrical discharge between the high voltage probe and a reference electrode at the location of an anomaly. As discussed above, when a high voltage probe energized with high voltage passes over an anomaly that penetrates the liner of the tire, an electrical discharge will occur between the high voltage probe and a reference electrode. Because the high voltage probe scans a particular radial position as a tire is azimuthally rotated about the high voltage probe, the precise radial and azimuthal location of an electrical discharge can be easily determined.

Once an electrical discharge is detected, an electrical signal representative of the location and occurrence of the electrical discharge can be provided to a computing device for analysis. For instance, in a particular embodiment, data can be collected for a fixed number of azimuthal points at each radial position on the surface of the tire. The data can include the radial position of the high voltage probe, the azimuthal location of the high voltage probe relative to the tire surface, and the binary state of a defect detection signal. The collected data can then be used to generate a graphical depiction of the tire surface, for instance, in the form of a two dimensional map or other suitable graphical depiction, for viewing and analysis by an operator.

Referring to FIGS. -7-, -8- and -9-, the operation of an exemplary automated tire testing apparatus 700 will be discussed in detail. Tire testing apparatus 700 includes a high voltage probe positioning device 710 configured to position a high voltage probe 720 adjacent the inner surface of a tire 702. High voltage probe 720 can include a conductive spring electrode adapted to be compressed against the surface of the tire. High voltage probe positioning device 710 is configured to move the high voltage probe 720 about a lateral axis 712, an extension axis 714, and a rotational axis 716.

In FIG. -7-, high voltage probe positioning device 710 has positioned high voltage probe 720 at a first radial location on the surface of tire 702. A tire rotation device can rotate the inner surface of tire 702 about high voltage probe 720 for at least one tire revolution after tire rotation device positioning device 710 has positioned high voltage probe 720 adjacent the inner surface of the tire 702. If an electronic discharge is detected from high voltage probe 720, a signal indicating the occurrence of an electrical discharge, as well as the radial and azimuthal position of the high voltage probe 710 can be sent to a computing device. For instance, a signal indicating that the electrical discharge occurred at the first radial position illustrated in FIG. -7- can be sent to a computing device.

After at least one tire revolution at the first radial position, tire rotation positioning device 710 can move the high voltage probe 720 to a second radial position. Preferably, the second radial position is immediately adjacent the first radial position to ensure the high voltage probe 720 scans the entire inner surface of tire 702. FIG. -8- illustrates the high voltage probe 720 at an exemplary second radial position on the inner surface of the tire. The second radial position illustrated in FIG. -8- is not located immediately adjacent to the first radial position of FIG. -7- and is illustrated at the crown portion of tire 702 for discussion purposes only. Those of ordinary skill in the art, using the disclosure provided herein, should understand that several radial positions, depending on the width of the conductive spring electrode used in the high voltage probe, are located between the first radial position of FIG. -7- and the second radial position of FIG. -8-.

Once the high voltage probe 720 has been positioned at the second radial position as illustrated at FIG. -8-, the tire rotation device can rotate the tire an additional time about high voltage probe 720. If an electronic discharge is detected between the high voltage probe 720 and a reference electrode, a signal indicating the occurrence of an electrical discharge at a second radial position can be sent to a computing device.

After at least one complete tire revolution at the second radial position, high voltage probe positioning device 710 can move the high voltage probe 720 to a third radial position as illustrated in FIG. -9-. The third radial position illustrated in FIG. -9- is not located immediately adjacent to the second radial position of FIG. -8- and is illustrated at the bead portion of tire 702 for discussion purposes only. Those of ordinary skill in the art, using the disclosure provided herein, should understand that several radial positions, depending on the width of the conductive spring electrode used in the high voltage probe 720, are located between the second radial position of FIG. -8- and the third radial position of FIG. -9-.

Once the high voltage probe 720 has been positioned at the third radial position as illustrated at FIG. -9-, a tire rotation device can rotate the tire an additional time about high voltage probe 720. If an electronic discharge is detected between the high voltage probe 720 and a reference electrode, a signal indicating the occurrence of an electrical discharge at the third radial position can be sent to a computing device. In this manner, the automated tire testing apparatus 700 can scan the entire inner surface of tire 702 and determine precise azimuthal and radial locations of any anomalies detected during the automated tire inspection process.

FIG. 10 illustrates an alternative reference electrode 175 that can be used in accordance with embodiments of the present disclosure. In contrast to the reference electrode 170 of FIG. -2-, the reference electrode 175 of FIG. -10- is maintained adjacent a bead portion 106 of tire 102. The reference electrode 175 includes a conductive spring member that is maintained adjacent the bead portion 106 of tire 102 as the tire 102 rotates about a high voltage probe. An electrical discharge between a high voltage probe and reference electrode 175 does not travel through the tread portion 104 of tire 102. Rather, an electrical discharge will travel from the high voltage probe through one or more carcass plies of the tire 102 to the bead portion 106 of tire 102. By providing a reference electrode 175 at the bead portion 106 of the tire 102, the electrical discharge will not be affected by any variations in tread thickness or chemical composition. This can decrease the number of false detections, leading to increased accuracy in the detection of tire surface anomalies. In addition, the providing the reference electrode 175 to the bead portion 106 of tire 102 can provide for a reduction in voltage applied to the high voltage probe from about 50 kV to about 37.5 kV.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A tire inspection apparatus, comprising:
a high voltage probe operable to be positioned adjacent a surface of a tire; a reference electrode;
a tire rotation device operable to impart relative motion between the surface of the tire and the high voltage probe; and
a detection circuit operable to detect one or more electrical discharges between the high voltage probe and the reference electrode;
wherein the high voltage probe comprises a conductive spring electrode configured to be compressed against the surface of the tire during a tire inspection process, the conductive spring electrode having a width such that successive positioning of the high voltage probe is required during the tire inspection process to scan the surface of the tire.

2. The tire inspection apparatus of claim 1, wherein said conductive spring electrode has a length sufficient to maintain contact with a point on the surface of the tire during a charge cycle for the high voltage probe.

3. The tire inspection apparatus of claim 2, wherein the length of said conductive spring electrode is about 50 mm.

4. The tire inspection apparatus of claim 1, wherein the apparatus further comprises a high voltage probe positioning device operable to position said high voltage probe adjacent the tire surface such that said conductive spring electrode is compressed against the surface of the tire at a first radial position.

5. The tire inspection apparatus of claim 4, wherein said high voltage probe positioning device is configured to adjust said high voltage probe from the first radial position on the surface of the tire to a second radial position on the surface of the tire.

6. The tire inspection apparatus of claim 1, wherein said high voltage probe comprises a plurality of adjacent conductive spring electrodes, each of said plurality of conductive spring electrodes configured to be compressed against a portion of the surface of the tire during a tire inspection process.

7. The tire inspection apparatus of claim 1, wherein the reference electrode comprises a conductive roller positioned adjacent a tread portion of the tire.

8. The tire inspection apparatus of claim 1, wherein the reference electrode is positioned adjacent a bead portion of the tire.

9. The tire inspection apparatus of claim 1, wherein the apparatus further comprises a detection circuit operable to provide a signal representative of the azimuthal and radial position of the one or more electrical discharges on the surface of the tire.

10. A tire inspection method, comprising:
positioning a high voltage probe adjacent a surface of a tire, the high voltage probe comprising a conductive spring electrode configured to be compressed against the surface of the tire;
energizing the high voltage probe;
imparting relative motion between the high voltage probe and the surface of the tire; and
detecting one or more electrical discharges between the high voltage probe and a reference electrode to detect the presence of one or more anomalies on the surface of the tire;
wherein imparting relative motion between the high voltage probe and the surface of the tire comprises:
positioning the high voltage probe such that the conductive spring electrode is compressed against the surface of the tire at a first radial position;
rotating with a tire rotation device the surface of the tire about the surface of the high voltage probe for at least one revolution;
positioning the high voltage probe such that the conductive ring electrode is compressed against the surface of the tire at a second radial position, the second radial position being adjacent to the first radial position; and
rotating with the tire rotation device the surface of the tire about the surface of the high voltage probe for at least one revolution.

11. The tire inspection method of claim 10, wherein imparting relative motion between the high voltage probe and the surface of the tire comprises rotating the surface of tire with a tire rotation device about the high voltage probe.

12. The tire inspection method of claim 10, wherein the method further comprises adjusting the radial position of the high voltage probe.

13. The tire inspection method of claim 10, wherein the conductive spring electrode has a length sufficient to maintain contact with a point on the surface of the tire during a charge cycle for the high voltage probe.

14. The tire inspection method of claim 10, wherein the method comprises monitoring the location of the one or more electrical discharges.

15. The tire inspection method of claim 10, wherein the method comprises positioning the reference electrode adjacent a tread portion of the tire.

16. The tire inspection method of claim 10, wherein the method comprises positioning the reference electrode adjacent a head portion of the tire.

17. A high voltage probe for use in a tire inspection apparatus, comprising: an insulating casing;
a spacing roller;
a high voltage connection point; and
a conductive spring electrode, the conductive spring electrode adapted to be compressed against a portion of a tire surface when said spacing roller contacts the surface of a tire
wherein the conductive spring electrode has a width such that successive positioning of the high voltage probe is required during the tire inspection process to scan the surface of the tire.

18. The high voltage probe of claim 17, wherein said conductive spring electrode has a length sufficient to maintain contact with a point on the surface of the tire during a charge cycle for the high voltage probe.

19. The high voltage probe of claim 17, wherein said conductive spring electrode has a length of about 50 mm.

* * * * *